(12) United States Patent
Smith et al.

(10) Patent No.: US 11,439,374 B2
(45) Date of Patent: Sep. 13, 2022

(54) DEVICES AND METHODS FOR ENDOSCOPIC PATCH DELIVERY

(71) Applicant: Boston Scientific Scimed, Inc., Maple Grove, MN (US)

(72) Inventors: Amanda Smith, Boston, MA (US); Andrew Pic, Northboro, MA (US); Hannah Rebar, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 250 days.

(21) Appl. No.: 16/525,888

(22) Filed: Jul. 30, 2019

(65) Prior Publication Data
US 2020/0038005 A1 Feb. 6, 2020

Related U.S. Application Data

(60) Provisional application No. 62/712,361, filed on Jul. 31, 2018.

(51) Int. Cl.
A61B 17/00 (2006.01)
A61L 24/08 (2006.01)
A61L 24/00 (2006.01)

(52) U.S. Cl.
CPC .... *A61B 17/00234* (2013.01); *A61L 24/0005* (2013.01); *A61L 24/08* (2013.01);
(Continued)

(58) Field of Classification Search
CPC .......... A61B 17/00234; A61B 17/0057; A61B 2017/00269; A61B 2017/00323;
(Continued)

(56) References Cited

U.S. PATENT DOCUMENTS 9,204,957 B2 12/2015 Gregory et al.
2012/0065674 A1 3/2012 Levy
(Continued)

FOREIGN PATENT DOCUMENTS

WO WO 2005/074814 8/2005

OTHER PUBLICATIONS

Denys, H. et al., "The extracellular matrix regulates cancer progression and therapy response: implications for prognosis and treatment," *Curr. Pharm. Des.*, vol. 15, pp. 1373-1384, 2009, abstract only.

(Continued)

*Primary Examiner* — Brooke Nicole Labranche
(74) *Attorney, Agent, or Firm* — Bookoff McAndrews, PLLC

(57) ABSTRACT

Systems and methods of delivering a patch to a target site of a patient are described herein. The patch may comprise a biomaterial such as chitosan or extracellular matrix and may be biocompatible and/or bioresorbable. The system may include an endoscope, a patch, and one of an instrument or a cap, the patch being coupled to the respective instrument or cap and detachable therefrom. Methods of delivering the patch to the target site may include introducing an endoscope into a gastrointestinal tract of a patient, e.g., the patch being in a folded or crimped configuration, navigating a distal end of the endoscope proximate a target site; and applying the patch to the target site while releasing the patch from the endoscope.

10 Claims, 7 Drawing Sheets

(52) U.S. Cl.
CPC ........... *A61B 2017/0034* (2013.01); *A61B 2017/00269* (2013.01); *A61B 2017/00323* (2013.01); *A61B 2017/00477* (2013.01); *A61B 2017/00557* (2013.01); *A61B 2017/00902* (2013.01); *A61B 2217/005* (2013.01); *A61B 2217/007* (2013.01)

(58) Field of Classification Search
CPC .. A61B 2017/0034; A61B 2017/00477; A61B 2017/00557; A61B 2017/0061; A61B 2017/00623; A61B 2017/00902; A61B 2217/005; A61B 2217/007; A61L 24/0005; A61L 24/08
See application file for complete search history.

(56) References Cited

U.S. PATENT DOCUMENTS

| | | | | |
|---|---|---|---|---|
| 2012/0143188 | A1* | 6/2012 | Gassivi | A61B 18/1492 606/49 |
| 2013/0079811 | A1* | 3/2013 | Agnew | A61B 17/0057 606/213 |

| | | | |
|---|---|---|---|
| 2017/0079717 | A1 | 3/2017 | Walsh |

OTHER PUBLICATIONS

Lu, P. et al. "Extracellular Matrix Degradation and Remodeling in Development and Disease," *Cold Spring Harb. Perspect. Biol.*, vol. 3, No. 12, pp. 1-24, Dec. 2011.

Mostow, E.N. et al., "Effectiveness of an extracellular matrix graft (OASIS Wound Matrix) in the treatment of chronic leg ulcers: a randomized clinical trial," *J. Vasc. Surg.*, vol. 41, pp. 837-843, May 2005.

Schaefer, L. et al., "Special issue: Extracellular matrix: Therapeutic tools and targets in cancer treatment," *Adv. Drug Deliv. Rev.* vol. 97, pp. 1-3, Feb. 2016, abstract only.

Schultz, G.S. et al., "Extracellular matrix: review of its roles in acute and chronic wounds," World Wide Wounds, Aug. 2005, available at http://www.worldwidewounds.com/2005/august/Schultz/Extrace-Matric-Acute-Chronic-Wounds.html (17 pages).

International Search Report for PCT/US/2019/044035 dated Nov. 15, 2019 (4 pages).

* cited by examiner

DEVICES AND METHODS FOR ENDOSCOPIC PATCH DELIVERY

CROSS-REFERENCE TO RELATED APPLICATIONS

This application claims the benefit of priority from U.S. Provisional Application No. 62/712,361, filed on Jul. 31, 2018, which is incorporated by reference herein in its entirety.

TECHNICAL FIELD

The present disclosure relates generally to medical devices and related methods of preparation and use thereof. More specifically, the present disclosure includes devices useful in endoscopic medical procedures, such as applying a patch to tissue for wound treatment.

BACKGROUND

Various medical procedures are used for treatment of tissue. For example, an endoscopic procedure may be performed to take tissue samples from the gastrointestinal tract or other organ systems for pathological evaluation and/or therapeutic purposes, such as detection and removal of pre-cancerous mucosal tissue or tumors. Endoscopic mucosal resection (EMR) and endoscopic submucosal dissection (ESD) may be used to separate upper tissue layers to assist in the removal of lesions. A consequence of such medical procedures can be a wound in need of repair and/or protection to allow for tissue repair. Other internal wounds or defects such as, e.g., inflammation, ulcerations, and the like, can result naturally and likewise benefit from therapeutic treatment. Medical devices in the form of bandages and dressings can be prepared from a variety of materials. Applying such dressings to internal tissue, e.g., in an endoscopic procedure, presents particular challenges.

SUMMARY OF THE DISCLOSURE

The present disclosure includes medical systems comprising a biocompatible patch and methods of use thereof, e.g., methods of delivering a patch to a target site of a patient. For example, the present disclosure includes a medical system that includes an endoscope defining at least one working channel and a patch comprising a biocompatible material. In some examples herein, the system further comprises (a) an instrument comprising a shaft slidably disposed in the working channel, the patch being coupled to, and releasable from, a distal end of the instrument; or (b) a cap coupled to a distal end of the endoscope, the patch covering a distal end of the cap and being releasable from the cap. In some examples, the patch comprises a biomaterial such as chitosan, e.g., chitosan acetate and/or chitosan lactate, extracellular matrix, or a combination thereof. Additionally or alternatively, the patch may have a thickness less than 3 mm, such as less than 2 mm or less than 1 mm. According to some aspects of the present disclosure, a least a portion of the patch comprises an adhesive, optionally a biocompatible and/or bioresorbable adhesive. In some examples, the patch is disposed inside the at least one working channel of the endoscope in a folded or crimped configuration. In other examples, the patch is coupled to an outer surface of the system, such as the outer surface of a cap coupled to the distal end of the endoscope.

In some examples wherein the system comprises the instrument, the distal end of the instrument is rotatable relative to the shaft of the instrument. Alternatively, the distal end of the instrument may be fixed to the shaft, such that rotation of the shaft causes a corresponding rotation of the distal end of the instrument. The distal end may have a cylindrical shape, for example and/or the distal end may include a balloon. In some examples, the distal end of the instrument includes a rim that inhibits or prevents proximal movement of the patch relative to the instrument. For example, the distal end of the instrument may include a cylinder and optionally a rim at or proximate the proximal end of the cylinder, e.g., to inhibit or prevent proximal movement of the patch relative to the cylinder and/or relative to the shaft of the instrument. In some examples, the distal end of the instrument includes a balloon, and the shaft of the instrument comprises an fluid channel in communication with the balloon. The fluid channel may be coupled to a source of fluid such as, e.g., water, air, or other inert gas.

In some examples wherein the system comprises the cap, the patch may be secured to an outer surface of the cap with a band, e.g., a flexible band, such as, e.g., an elastic band. According to some aspects of the present disclosure, the cap includes a ridge on an outer surface of the cap. Additionally or alternatively, the cap may have a frustoconical shape. In some examples, the distal end of the endoscope includes an optical device, and the patch includes an opening aligned with the optical device. Additionally or alternatively, at least a portion of the patch covering the optical device may be translucent. In some examples, the entire patch is translucent.

The endoscope of the system may comprise a single working channel or a plurality of channels. In some examples, the system comprises an auxiliary instrument insertable in one or more of the working channels, e.g., to assist in applying the patch to tissue. Such auxiliary instruments may include, for example, a forceps or other instrument to assist in manipulating the patch relative to the target site. In some examples, the endoscope includes a suction channel in communication with a source of suction and/or a fluid channel in communication with a source of fluid such as air or water.

Also disclosed herein is a method of delivering a patch to a target site of a patient, the method comprising introducing an endoscope into a gastrointestinal tract of a patient, wherein the endoscope includes a patch in a folded or crimped configuration, the patch comprising a biocompatible material; positioning a distal end of the endoscope proximate a target site; and applying the patch to the target site while releasing the patch from the endoscope. The target site may include wounded or diseased tissue, for example, or the target site may correspond to the site of a prior medical procedure. In some examples, the target site includes a laceration in tissue following endoscopic mucosal resection (EMR), endoscopic submucosal dissection (ESD), or tissue biopsy. In some examples, wherein the target site includes an anastomosis, e.g., such that the patch inhibits or prevents leakage. As mentioned above, the patch may comprise a biomaterial such as chitosan, e.g., chitosan acetate and/or chitosan lactate, extracellular matrix, or a combination thereof; and/or the patch may comprise an adhesive, such as, e.g., a biocompatible and/or bioresorbable adhesive.

According to some aspects of the present disclosure, the method further comprises introducing an instrument comprising a shaft into a working channel of the endoscope, the patch being disposed on a distal end of the instrument. For example, applying the patch to the target site may include unrolling the patch from the distal end of the instrument. Further, for example, the distal end of the instrument may include a cylinder, the patch being disposed on a surface of the cylinder, wherein applying the patch to the target site includes rotating the cylinder, e.g., relative to the target site and/or relative to the shaft of the instrument. In at least one example, the cylinder includes a rim that prevents proximal movement of the patch relative to the shaft.

In some examples, the distal end of the instrument includes a balloon, and the shaft of the instrument comprises a fluid channel in communication with the balloon, e.g., for inflation and deflation of the balloon. For example, the patch may be disposed on a surface of the balloon in a folded configuration, the method comprising expanding the balloon to unfold the patch, e.g., to apply the patch to the target site.

As mentioned above, in some examples herein, the endoscope includes a cap coupled to a distal end of the endoscope, the patch covering a distal end of the cap and being releasable from the cap. Thus, for example, applying the patch to the target site may include releasing the patch from the cap, optionally by applying pressure to the patch with a fluid (e.g., air or water) and/or with an instrument via a working channel of the endoscope.

Also provided herein is a method of delivering a patch to a target site of a patient, the method comprising introducing a system comprising an endoscope into a gastrointestinal tract of a patient, wherein the system includes a patch comprising a biocompatible material and one of (a) an instrument comprising a shaft slidably disposed in a working channel of the endoscope, the patch being coupled to, and releasable from, a distal end of the instrument; or (b) a cap coupled to a distal end of the endoscope, the patch covering a distal opening of the cap and being releasable from the cap. The method may further comprise positioning a distal end of the endoscope proximate a target site; and applying the patch to the target site while releasing the patch from the system. In some examples, the patch is coupled to the distal end of the instrument or the cap in a folded or crimped configuration. According to some aspects, releasing the patch includes blowing air or spraying water from a channel of the endoscope onto the patch. In some examples herein, the distal end of the instrument includes a cylinder that comprises a rim, the patch being disposed on a surface of the cylinder distal to the rim.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Figure 1:
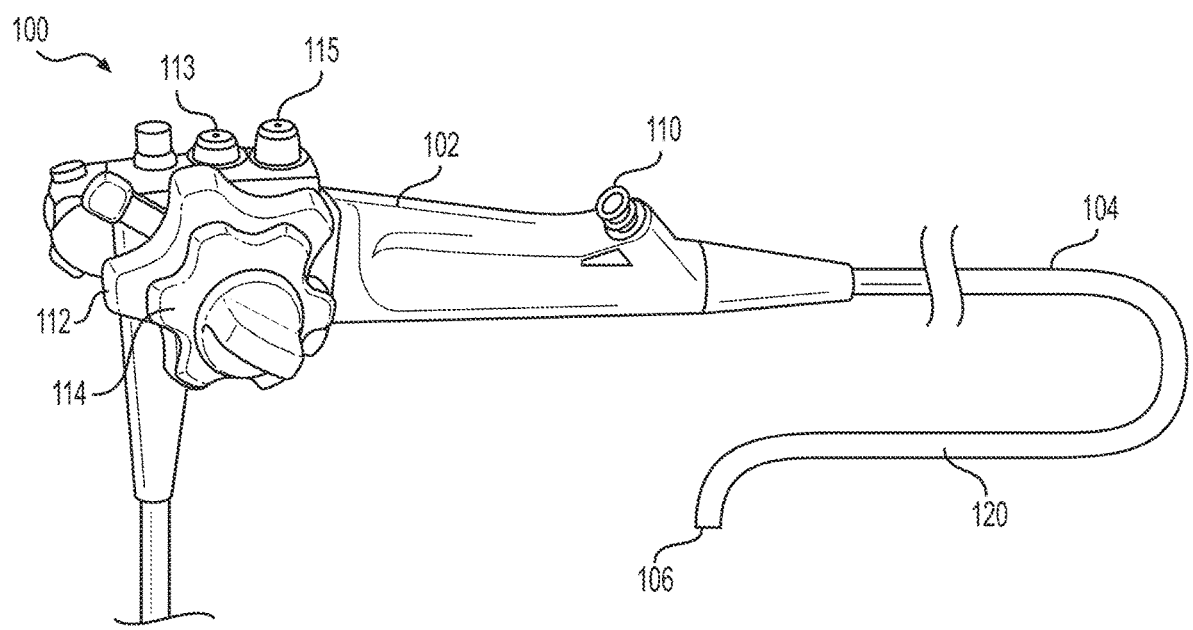
FIG. 1 shows an exemplary endoscope, in accordance with some aspects of the present disclosure.

Particular aspects of the present disclosure are described in greater detail below. The terms and definitions provided herein control, if in conflict with terms and/or definitions incorporated by reference.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal."

As used herein, the singular forms "a," "an," and "the" include plural reference unless the context dictates otherwise. The terms "approximately" and "about" refer to being nearly the same as a referenced number or value. As used herein, the terms "approximately" and "about" should be understood to encompass ±5% of a specified amount or value.

Embodiments of the present disclosure include medical systems and methods for endoscopic delivery of patches for treating tissue. The patches herein may comprise one or more biomaterials (e.g., materials that are biocompatible and/or derived from biological materials), which may be at least partially or completely bioresorbable. For example, upon application to tissue, at least a portion of the patch may dissolve and/or be absorbed by the body over time. In some cases, a portion of the patch may be shed from the site of application to be absorbed or removed by the gastrointestinal system.

The patches herein may serve as a protective layer, a barrier against leaks, a barrier against perforations, a defect closure, a scaffold to promote cell growth, and/or as a hemostatic agent, among other uses. Further, for example, the patches herein may be used to treat various types of tissues, including wounded or diseased tissue, such as burns, lacerations, lesions, inflammation, ulceration, perforations, microperforations, and other sites in need of treatment or repair. The patches herein may be used as an alternative to, or in combination with, sutures, staples, adhesive, and other methods for securing or protecting tissue. In at least one example, the patch may be applied to serve as a hemostatic agent, e.g., to prevent or inhibit bleeding of tissue at a target site.

Exemplary sites to which the patches herein may be applied include, but are not limited to, tissues of the gastrointestinal system such as, e.g., the esophagus, the stomach, the small intestine (e.g., duodenum, jejunum, or ileum), and/or the large intestine (e.g., cecum, colon, rectum, or anal canal). In some examples, an anastomotic resection of the small or large intestine may lead to a risk of leaks between suture lines. The patches herein may be applied to such junctions to serve as a barrier against leakage. In some examples, the patches herein may be applied to a fistula, e.g., an intestinal fistula, to serve as a barrier against leakage of fluid and/or to cover a sac to prevent it from boring into surrounding anatomy Further, for example, the patches herein may be useful for patients that have inflammatory bowel disease (IBD), e.g., applying the patch to a subsidiary disease fistula associated with IBD, wherein the fistula connects intestinal lumens.

In some examples herein, the patch is delivered endoscopically, optionally in conjunction with a medical procedure such as endoscopic mucosal resection (EMR), endoscopic submucosal dissection (ESD), or tissue biopsy. For example, a patch may be delivered endoscopically to a target site to assist the body in regrowing tissue layers removed via ESD or due to ulceration of the mucosal layer. Exemplary biomaterials suitable for the patches herein include, but are not limited to, chitosan, extracellular matrix (ECM), and other biomaterials comprising structural polysaccharides, and combinations thereof.

In some examples herein, the patch comprises chitosan. Chitosan is a linear polysaccharide formed of glucosamine units derived from chitin, the structural component of crustacean exoskeletons.

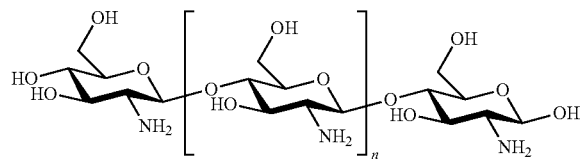

Chitosan is typically prepared by deacetylation of chitin with an alkaline reagent such as sodium hydroxide, yielding a water-soluble material. Chitosan is antimicrobial and has natural bioadhesive properties that allows it to bind to negatively charged surfaces such as mucosal membranes.

The patches herein may comprise chitosan in the form of a salt. For example, salts may be prepared by combining chitosan with a suitable conjugate acid such as acetic acid (forming chitosan acetate) or lactic acid (forming chitosan lactate). Other possible organic acids include, but are not limited to, succinic acid (chitosan succinate), glutamic acid (chitosan glutamate), glycolic acid (chitosan glycolate), and citric acid (chitosan citrate). In an exemplary procedure to prepare a chitosan salt, chitosan is suspended in water at room temperature, followed by the addition of an organic acid (e.g., acetic acid and/or citric acid) to form a gel. The gel is then dried into a film or sheet of desired thickness and dimensions. Without intending to be bound by theory, it is believed that the acid provides for a cross-linked structure that provides sufficient integrity and strength for use as a protective layer when applied to tissue.

In some examples herein, the patch comprises extracellular matrix (ECM). ECM is a complex and naturally-occurring structural material found within tissues that surround and support cells within tissues and organs of living creatures. It makes up the area external to cells and provides physical scaffolding as well as biochemical and biomechanical cues that direct cell function. ECM has been described as the glue that holds cells within a tissue together. ECM typically comprises structural proteins and polysaccharides, as well as various growth factors. ECM materials can provide a generally dynamic structure that adapts to fit the surrounding environment.

The chemical composition of ECM can vary depending on its source, e.g., the type of tissue from which it is derived. For example, ECM may be derived from various types of collagenous tissue. ECM suitable for the present disclosure may be derived from any suitable types of tissue, including, but not limited to, tissues of the spleen, kidney, liver, lung, pancreas, gall bladder, or stomach. Further, the tissue may be obtained from various types of native tissues including, but not limited to, porcine, bovine, ovine, and human tissue.

The patches herein may be formed into any suitable shape and dimensions, e.g., based on the nature of the target tissue site. In some examples, the thickness of the patch may be on the order of millimeters, e.g., ranging from about 0.1 mm to about 5.0 mm, from about 0.2 mm to about 3.0 mm, from about 0.5 mm to about 2.0 mm, or from about 0.8 mm to about 1.0 mm, e.g., a thickness of about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, or about 1.5 mm. In at least one example, the thickness of the patch is less than 3 mm, less than 2 mm, less than 1 mm, or less than 0.5 mm. According to some aspects of the present disclosure, the thickness may be uniform. The patches herein may be at least partially translucent in some cases, e.g., allowing light to pass therethrough. The patch may have any shape such as, e.g., square, rectangular, oval, circular, among other possible shapes. In some examples, the patch has a tubular shape, e.g., a thin-walled cylinder, suitable for application to a body lumen such as the esophagus or small or large intestine.

The patches according to the present disclosure may be pliable and bendable. For example, the patch may be formed into a planar film, sheet, or disc capable of being folded, crimped, or otherwise manipulated into a temporarily non-planar configuration within a confined space. Thus, for example, the patch may be folded, curved, or crimped within a confined enclosure such as a sheath or lumen for suitable delivery via an endoscope. Once released, the patch may recover its original planar configuration.

The patch may be substantially dry during delivery to a target site. In some examples herein, the patch may be moistened during delivery or shortly following release from a delivery instrument. For example, the patch may be exposed to water via a fluid channel of an endoscope and/or through contact with bodily fluids or humidity inside the body. When exposed to moisture, the patch may absorb the fluid, causing the patch to swell or expand. For example, the patch, when dry, may be substantially paper-like, and when wet, may take on a more jelly-like consistency. According to some aspects of the present disclosure, moistening the patch may assist in its application to tissue.

In some examples herein, the patch comprises an adhesive, e.g., to assist in applying the patch to tissue and/or maintaining the patch in place after application, and/or to assist in delivery of the patch to the target site. Adhesives suitable for the present disclosure may be natural, e.g., comprising a natural polymer or derived from a natural polymer, or synthetic. Exemplary adhesives include, but are not limited to, gelatin (including, e.g., thrombin/gelatin), fibrin (e.g., fibrin glue), cyanoacrylate, polyethylene glycol (PEG), and albumin (including, e.g., albumin glutaraldehyde). The adhesive may be at least partially resorbable.

The choice of adhesive may be at least partially based on the desired adhesion strength, bioresorbable properties, and/or the nature of the target site to which the patch is being applied. For example, a relatively stronger adhesive may be desired for a patch comprising ECM than for a patch comprising chitosan, which has natural bioadhesive properties. Further, for example, a patch intended for application to a relatively large wound or defect site, may comprise adhesive to further assist with securing the patch to the tissue. Patches according to the present disclosure may comprise adhesive applied to one area or two or more areas, e.g., opposing ends. In some examples, the patch does not include an adhesive.

Medical systems according to the present disclosure may comprise an instrument or cap providing a surface for delivery of a patch comprising a biomaterial or combination of biomaterials as described above and/or elsewhere herein. The systems herein may comprise an endoscope, the patch or patches to be delivered, and/or one or more auxiliary instruments such as, e.g., forceps, an imaging device, or an optical device, etc. The patch or patches may be delivered through the working channel of an endoscope, for example, or with the assistance of a cap coupled to the distal end of an endoscope.

FIG. 1 shows an exemplary endoscope 100 useful for some aspects of the present disclosure, the endoscope 100 including a controller 102 and a shaft 104 extending distally from the controller 102 to a distal end 106. The controller 102 may have any suitable shape and steering mechanism(s) to allow an operator to navigate the shaft 102 through tortuous anatomy and/or towards a site of interest. Accordingly, the shaft 104 may be sufficiently flexible to maneuver through different anatomical structures, including portions of the gastrointestinal system.

Any suitable steering mechanism may be used. For example, the steering mechanism may comprise a plurality of steering wires coupling the controller 104 to the shaft 102, e.g., to transmit user input from the controller 102 to the shaft 104 to articulate or deflect the shaft 104 along one or more planes. As shown in FIG. 1, for example, the controller 102 may include one or more actuators, e.g., first and second actuators 112, 114 to control deflection of the distal end 106 of the shaft 104 in two different planes, e.g., along the xy plane via actuator 112 and along the yz plane via actuator 114. Concerted movement of the actuators 112, 114 may achieve deflection in a plurality of other planes, e.g., providing for 360 degree manipulation of the shaft 104. Other steering mechanisms suitable for manipulating the shaft 102 may be used, including, but not limited to, other types of mechanical mechanisms and electrical mechanisms. For example, the controller 102 may be in electrical communication with various portions of the shaft 104, such that user input at the actuator 112, 114 may be converted to electrical signals to control deflection of the distal end 106 of the shaft 104.

Figure 7:
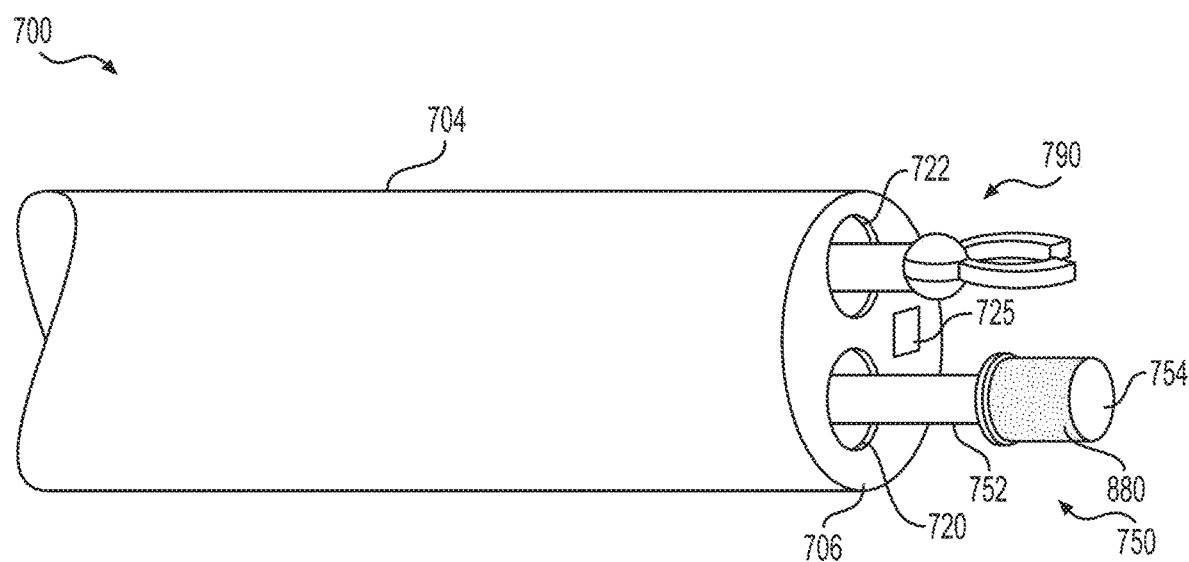
FIG. 7 shows an exemplary system, in accordance with some aspects of the present disclosure.

The shaft 104 may include one or more working channels (e.g., working channel 120) in communication with one or more corresponding ports (e.g., port 110) of the controller 102. One or more instruments may be inserted into the working channel 120 via the port 110 for performing a medical procedure. Exemplary instruments include, but are not limited to, the instruments illustrated in FIGS. 2A-2C, 3A-3D, 5A-5D, and 7 (discussed below), and/or other instruments such as forceps, scissors, scalpels, snares, biopsy brushes, optical devices, or imaging devices. In some examples, the controller 102 includes only one port 110 or may include two or more ports each in communication with a separate working channel (see, e.g., working channels 720 and 722 in FIG. 7). In some examples, the controller 102 may include controls for suction and/or fluids such as a suction valve 113 and a fluid valve 115. Thus, for example, the suction valve 113 may be in communication with a suction channel of the shaft 104 and the fluid valve 115 may be in communication with a fluid channel of the shaft 104.

Figure 2A:
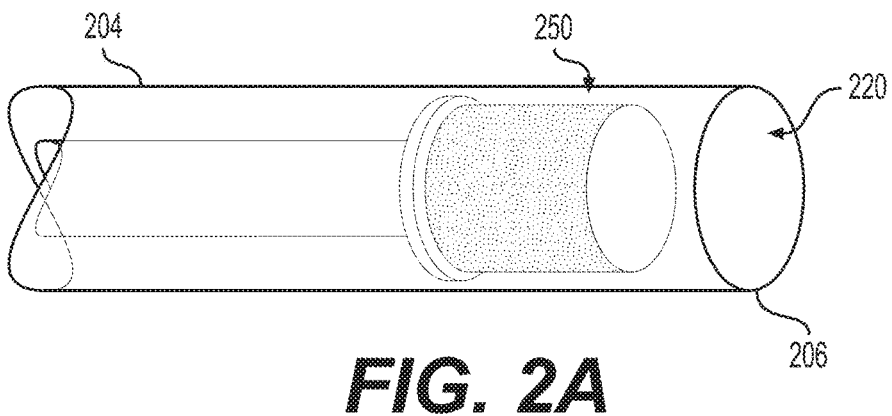
FIGS. 2A-2C illustrate delivery of a patch with an exemplary system, in accordance with some aspects of the present disclosure.
Figure 2B:
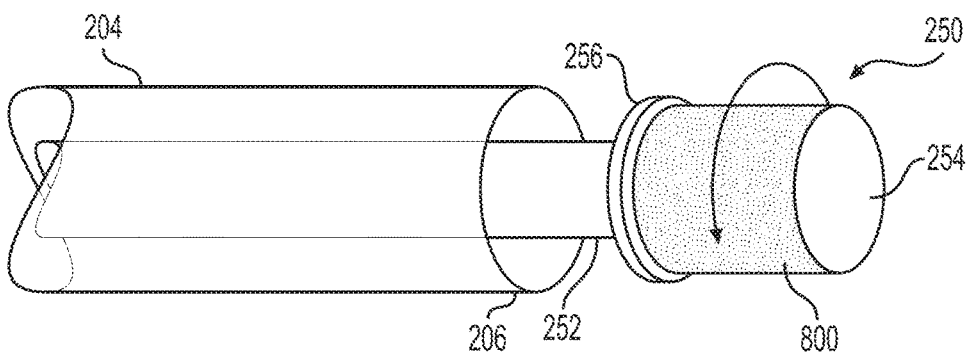
Figure 2C:
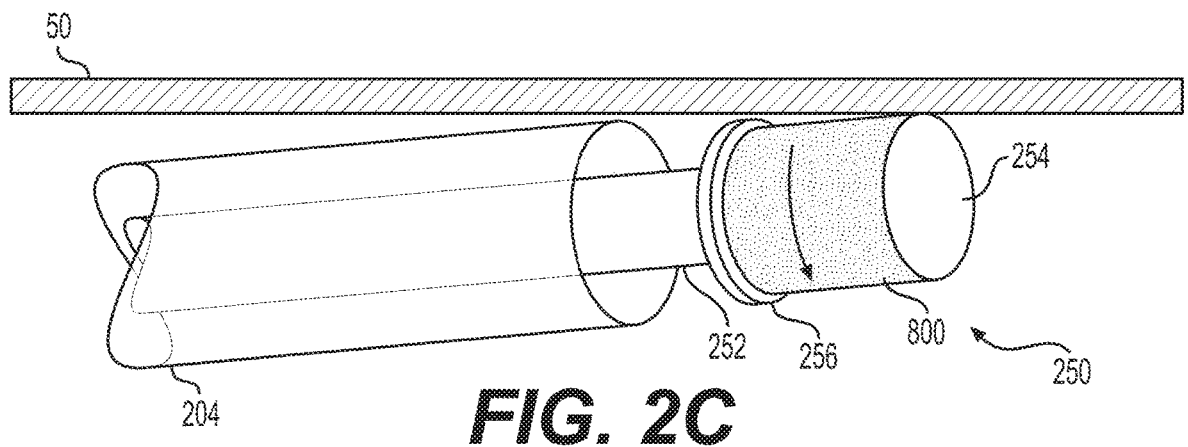

FIGS. 2A-2C illustrate an exemplary system comprising a delivery instrument 250 and method of delivering a patch to a target site using the system, according to some aspects of the present disclosure. Specifically, the instrument 250 is shown disposed within the working channel 220 of an endoscope shaft 204 extending to distal end 206. While only one working channel is shown, the method illustrated is equally applicable to an endoscope having a plurality of working channels, one of which houses the instrument 250. Instrument 250 includes a shaft 252 and a cylinder 254 at the distal end of the shaft 252, e.g., similar to a drum or a spool. In some examples, the cross-section of the cylinder 254 may be greater than the cross-section of the shaft 252.

According to some aspects of the present disclosure, the cylinder 254 is rotatable relative to the shaft 252. For example, the cylinder 254 may be free-moving and capable of free rotation relative to the shaft 252, similar to a wheel. Alternatively, the instrument 250 may include a mechanism to provide for controlled rotation of the cylinder 254, such as a mechanical lever or electronic switch coupled to the cylinder 254 via the shaft and located on a proximal handle of the instrument 250 (e.g., the handle being proximal to the port of the endoscope, e.g., port 110 of FIG. 1). In some examples, the cylinder 254 may be fixed relative to the shaft 252, such that rotation of the shaft 252 relative to the working channel 220 causes corresponding rotation of the cylinder 254.

The dimensions of the cylinder 254 may be selected to accommodate a patch 800 radially between the outer surface of the cylinder 254 and the inner surface of the working channel 220. That is, the patch 800 may be wrapped or otherwise disposed on the outer surface of the cylinder 254. The proximal end of the cylinder 254 as shown includes a raised surface, e.g., rim 256, to help maintain the position of the patch 800 and to prevent proximal movement of the patch 800 as the instrument 250 slides along the working channel 220. The rim 256 is an annular flange having an outer diameter greater than the outer diameter of the cylinder 254. Additionally or alternatively, the surface of the patch 800 in contact with the cylinder 254 may include an adhesive to secure the patch 800 to the instrument 250. The adhesive may be chosen to have a strength sufficient to prevent movement of the patch 800 relative to the instrument during delivery while allowing for release of the patch 800 upon contact of the patch 800 with tissue.

In some examples, the system may include a catheter or sleeve between the instrument 250 and the working channel 220. For example, the catheter or sleeve may be disposed radially outside the shaft 252 (and the cylinder 254 and the patch 800 disposed on the cylinder 254), and the inner surface of the working channel 220, e.g., to protect the patch 800 during delivery. In such cases, the instrument 250 may be preloaded through the protective catheter/sleeve to prevent the patch 800 from moving, the instrument 250 then moved distally relative to the catheter/sleeve to deploy the patch 800. An adhesive as discussed above may additionally be used, or the catheter/sleeve may be sufficient to maintain the position of the patch 800 prior to deployment, without an adhesive.

During delivery, the instrument 250 is initially entirely disposed within the working channel 220 as shown in FIG. 2A. Once the shaft 204 is proximate the tissue wall 50 that includes the target site, the instrument 250 may be moved distally to exit the working channel 220 as shown in FIG. 2B. The shaft 204 and/or the instrument 250 then may be manipulated to allow the patch 800 to contact the tissue wall 50 at or adjacent to the target site as shown in FIG. 2C. The portion of the patch 800 in contact with the tissue wall 50 may attach to the tissue (optionally with the assistance of an adhesive) and release from the surface of the cylinder 254 while the remainder of the patch 800 remains disposed on the cylinder 254. The cylinder 254 then may be rotated about a longitudinal axis of the cylinder 254 relative to the tissue wall 50, to apply the remainder of the patch 800 to the tissue wall 50, including covering the target site, while releasing (e.g., unwinding) the patch 800 from the cylinder 254.

The patch 800 may be secured to the tissue wall 50 with or without an adhesive. For example, the biomaterial of the patch itself may have adhesive properties and/or may preferentially adhere to the tissue. In some examples, an auxiliary instrument such as a forceps may be used to assist in removing the patch 800 from the instrument 250 and/or applying the patch 800 to the tissue wall 50. See, e.g., FIG. 7 discussed below.

FIGS. 3A-3D illustrate another exemplary system and method of delivering a patch according to some examples of the present disclosure. Specifically, an instrument 350 is shown disposed within the working channel 320 of an endoscope shaft 304 extending to a distal end 306. Again, only one working channel is shown for illustration purposes, however, the method illustrated is equally applicable to an endoscope having a plurality of working channels. Instrument 350 as shown includes a shaft 352 that terminates in a distal end 354.

Figure 3A:
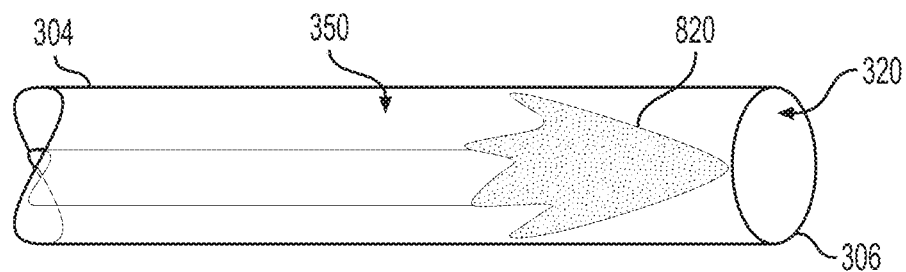
FIGS. 3A-3D illustrate delivery of a patch with an exemplary system, in accordance with some aspects of the present disclosure.

During delivery, the instrument 350 is initially entirely disposed within the working channel 320 as shown in FIG. 3A. A patch 820 formed as a film or sheet may be disposed on the distal end 354 of the shaft 352 in a folded, crimped, or collapsed configuration suitable for delivery. For example, the patch 820 may be sufficiently pliable to allow the patch 820 to be folded in the confined space of the working channel 320 but then unfold when released from the working channel 320. As shown in FIG. 3A, the patch 820, much like an umbrella, extends proximally around the shaft 352 with its edges positioned proximal to the distal end 354 of the shaft 352 and radially between the outer surface of the shaft 252 and the inner surface of the working channel 320.

Figure 3B:
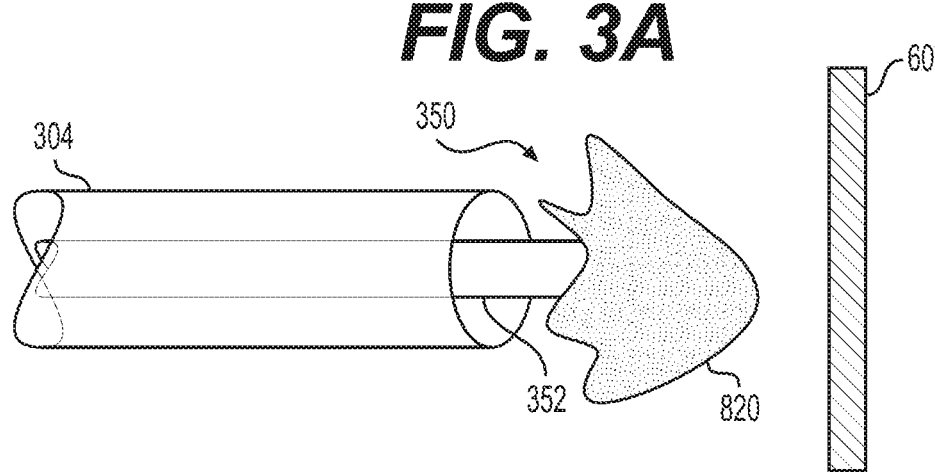
Figure 3C:
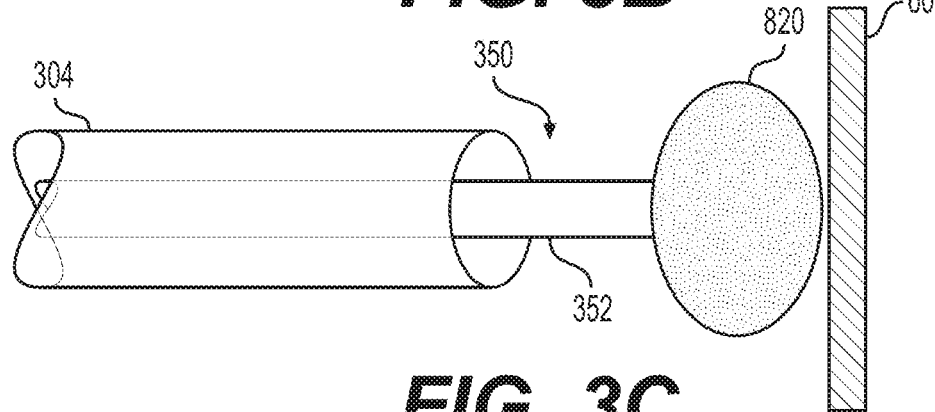
Figure 3D:
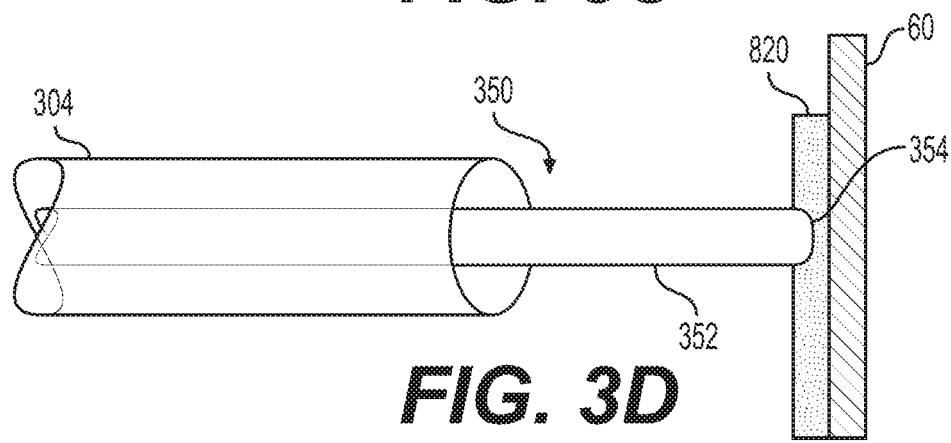

Once the distal end 306 of the endoscope shaft 304 is proximate the target site, e.g., facing the tissue wall 60 that contains the target site as shown in FIG. 3B, the instrument 350 may be moved distally to exit the working channel 320. As the patch 820 is released from the working channel 320, the edges of the patch 820 may unfold as shown in FIGS. 3B and 3C, e.g., the patch 820 being sufficiently flexible to adopt the folded configuration inside the working channel 320 but recovering its original, unfolded configuration when unconstrained. For example, the edges of the patch 820 may unfold or expand when unconfined from the working channel 320 to recover the original, unfolded configuration of the patch 820, as shown in FIG. 3C. Finally, the instrument 350 may be further advanced distally to apply the patch to the tissue wall 60, thus covering the target site. In some cases, the patch 820 may be sufficiently adhered to the distal end 354 of the shaft 352, e.g., with an adhesive to allow the patch 820 to remain secured to the instrument 350 until it comes into contact with the tissue wall 60. Pressure then may be applied to the patch 820 with the shaft 352 to secure the patch 820 to the tissue wall 60. In some examples, the patch 820 may preferentially adhere to the tissue wall 60. In some examples, an auxiliary instrument such as a forceps may be used to assist in removing the patch 820 from the instrument 350. Further, in some examples, water and/or positive air pressure may be applied to the patch 820 to assist in application to the tissue wall 60. In cases where water is introduced through the working channel 320 or another channel of the endoscope, e.g., a fluid channel, the patch 820 may absorb the fluid and expand. Moistening the patch 820 may enhance its ability to preferentially attach to the tissue wall 60.

Figure 4A:
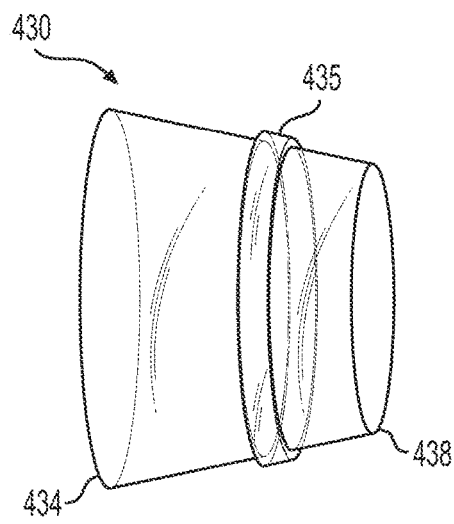
FIG. 4A shows an exemplary endoscope cap.

FIG. 4A shows a cap 430 that may be used in some methods herein. The cap 430 defines a lumen and extends from a proximal end 434 to a distal end 438 in a generally frustoconical shape. The outer surface of the cap 430 includes a raised portion, e.g., ridge 435, which may extend circumferentially along the cap 430 in a direction perpendicular or transverse to the length of the cap 430. In some examples, the ridge 435 may extend along only a portion of the circumference of the cap 430 and/or the ridge 435 may be configured as a plurality of raised surfaces generally arranged in a circumferential pattern. According to some aspects of the present disclosure, the cap may be at least partially or completely transparent. In other examples, the cap may be at least partially or completely opaque.

Figure 4B:
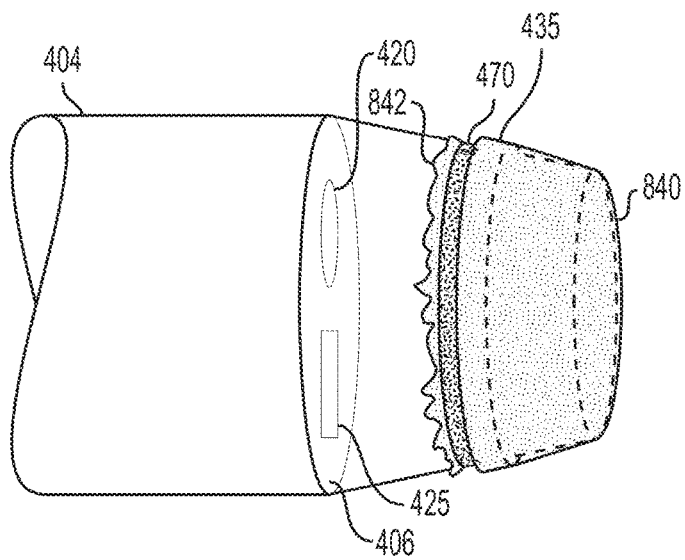
FIGS. 4B and 4C illustrate delivery of a patch using the endoscope cap, in accordance with some aspects of the present disclosure.
Figure 4C:
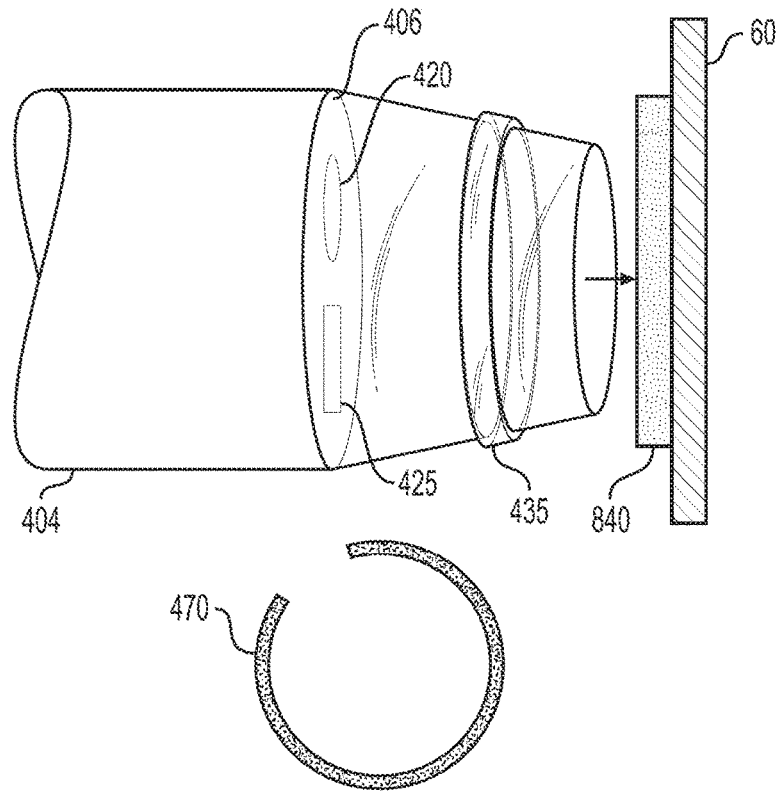

The proximal end 434 of the cap 430 is configured to fit onto the distal end of an endoscope, e.g., distal end 406 of endoscope shaft 404 in FIGS. 4B and 4C. Any suitable method or features for attaching the cap 430 to the endoscope may be used. For example, the cap 430 may be formed of a flexible material, e.g., flexible plastic, such that the proximal end 434 of the cap 430 may surround the distal end of the endoscope in a tight, friction fit. Other possible features include, but are not limited to, tabs or threads. A patch 840 is coupled to the distal end 438 of the cap 430, such that the patch 840 extends across, and covers, the distal opening of the lumen of the cap 430. The patch 840 may extend proximally, such that a portion of the patch 840 extends over the ridge 435 with the edges 842 of the patch 840 proximal to the ridge 435. A band 470 is disposed on the proximal side of the ridge 435, over the patch 840 as shown in FIG. 4B, to secure the patch 840 in place and prevent distal movement of the patch 840 relative to the cap 430. In some examples, the patch 840 may extend further proximal to the ridge 435 than shown in FIG. 4B, e.g., closer to the distal end 406 of the endoscope shaft 404. The band 470 may be elastic and flexible, e.g., comprising a material such as plastic or silicone. In some examples, the endoscope may include an optical device 425 to assist in viewing the target site during delivery. In some examples, the portion of the patch 840 that overlays the optical device 425 may be cut to allow a window through which a user may see the tissue wall 60 via the optical device 425.

To deliver the patch 840 to the target site of a tissue wall 60, the cap 430 may be coupled to the distal end 406 of the endoscope with the patch 840 and band 470 attached as described above. Once the distal end 406 is proximate the target site, e.g., facing the tissue wall 60 that contains the target site as shown in FIG. 4C, the endoscope may be moved distally to press the patch 840 against the tissue wall 60, such that the patch 840 covers all or some of the target site. In order to release the patch 840 from the cap 430, the band 470 may be cut so that it uncovers the patch 840. For example, the band 470 may be attached to a mechanism of deployment affixed temporarily, for the purposes of the procedure, to the working channel, handle, or other portion of the endoscope, such that a user may actuate/tighten the wire to cut the band 470, e.g., via a suitable actuator (e.g., knob, wheel, gear, button, pull-tab, etc.) attached or otherwise coupled to the wire. In some examples, the wire may be tied to the band and extend distally alongside the endoscope shaft or through the a working channel 420 of the endoscope, e.g., the wire passing through a hole in the cap 430 or an opening between the cap 430 and the distal end 406 of the endoscope. A portion of the band 470 may be tethered to the cap 430 and/or the endoscope to avoid loss of the band 470 during delivery of the patch 840.

In some cases, the pressure applied to the patch 840 with the endoscope in combination with release of the band 470 may be sufficient to entirely release the patch 840 from the endoscope and cap 430. Additionally or alternatively, insufflation and/or water pressure may be used to decouple the patch 840 from the cap 430 by blowing air or spraying water from a fluid channel of the endoscope against the side of the patch 840 facing the endoscope.

FIGS. 5A-5D illustrate yet another exemplary system and method according to some aspects of the present disclosure. Specifically, an instrument 550 is shown disposed within the working channel 520 of an endoscope shaft 504 extending to a distal end 506. Only one working channel is shown for illustration purposes, however, the method illustrated is equally applicable to an endoscope having a plurality of working channels. Instrument 550 includes a shaft 552 coupled to an inflatable device, e.g., balloon 556. The shaft 552 may include a fluid channel, e.g., coupled to a source of fluid such as air or water, in communication with the balloon 556 for inflation and deflation.

A patch 860 is disposed on the outer surface of the balloon 556, e.g., in a folded or crimped state, while the balloon 556 is deflated. The folds may allow for the patch 860 to accommodate expansion of the balloon 556. In some examples, the patch 860 may have a tubular shape and completely surround the balloon 556, as shown. In other examples, the patch 860 may be configured as a film or sheet disposed on only a portion of the circumference of the balloon 556.

Figure 5A:
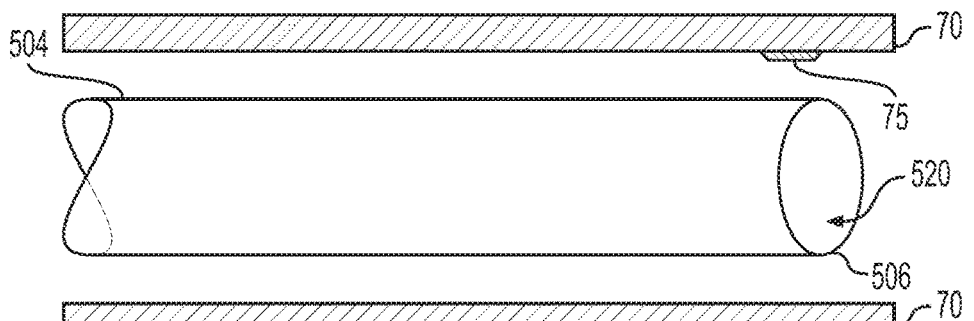
FIGS. 5A-5D illustrate delivery of a patch with an exemplary system, in accordance with some aspects of the present disclosure.
Figure 5B:
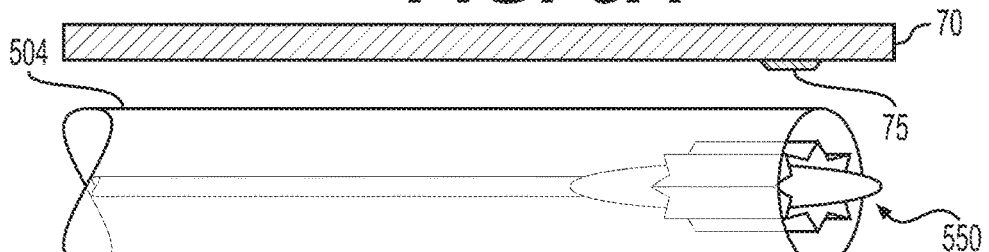
Figure 5C:
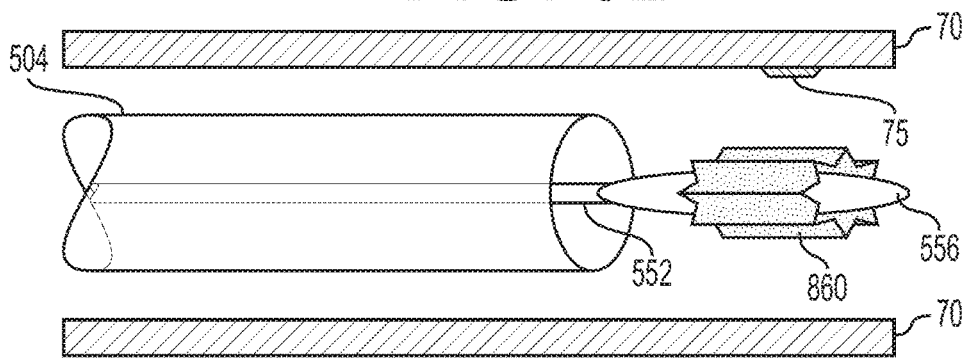
Figure 5D:
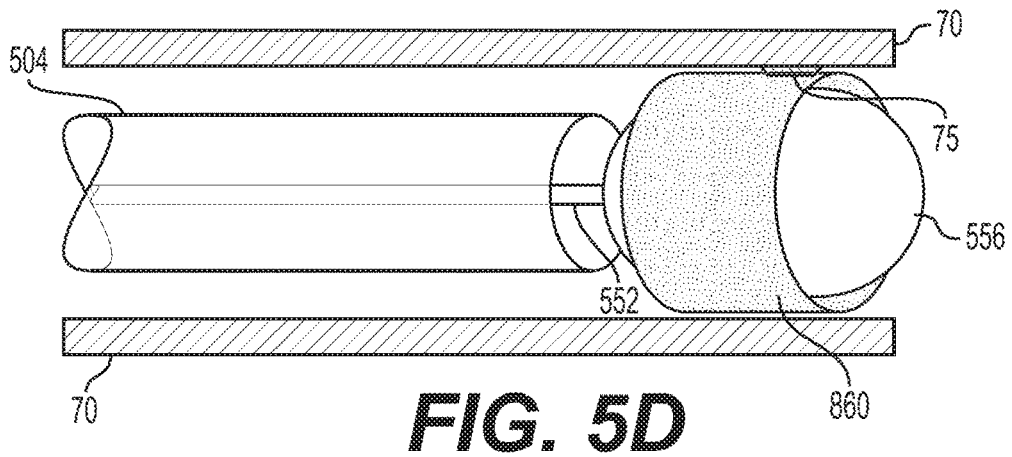

During delivery, the endoscope is inserted into a body lumen adjacent to a tissue wall 70 that includes a target site 75, such as a lesion or other wound. The instrument 550 is initially entirely disposed within the working channel 520 as shown in FIG. 5A. Once the shaft 504 of the endoscope is proximate the target site 75, the instrument 550 may be moved distally to exit the working channel 520, as shown in FIG. 5B. The instrument 550 is advanced, or the endoscope is retracted or withdrawn, such that the balloon 556 and patch 860 disposed thereon, are outside the working channel 520, as shown in FIG. 5C. Finally, the balloon 556 is inflated, thus expanding and unfolding the patch 860 such that the patch 860 contacts the tissue wall 70 and the target site 75, as shown in FIG. 5D. Upon contacting the tissue, the patch 860 may preferentially attach to the tissue and release from the balloon 556. In some examples, the patch 860 may be secured to the balloon 556 with an adhesive with sufficient strength to prevent movement of the patch 860 relative to the balloon 556 during delivery while allowing for release of the patch 860 upon contact with the tissue wall 70. Once the patch 860 is released, the balloon 556 may be deflated and the instrument 550 and endoscope withdrawn from the body lumen.

Figure 6A:
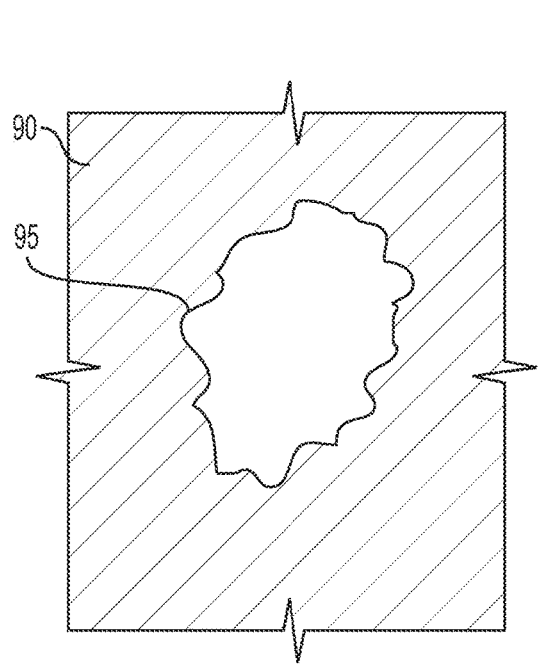
FIGS. 6A-6C illustrate delivery of a patch with an exemplary system, in accordance with some aspects of the present disclosure.
Figure 6B:
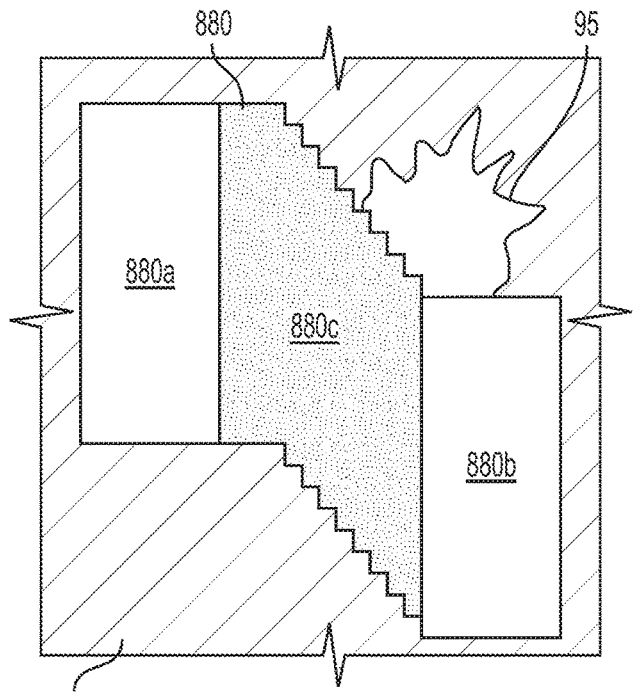
Figure 6C:
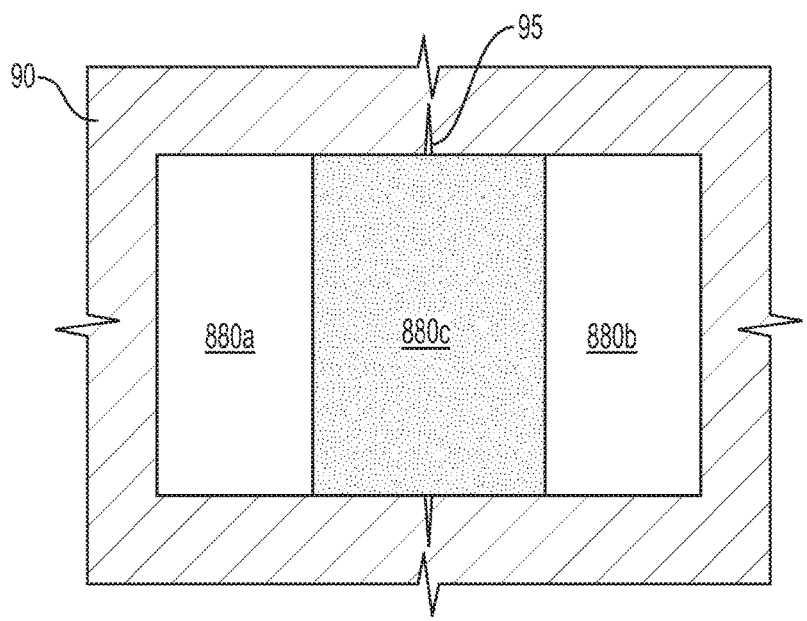

FIGS. 6A-6C illustrate another example of applying a patch 880 to a tissue wall 90 of a patient. For example, the tissue wall 90 may be part of the patient's gastrointestinal system, such as the esophagus, the stomach, the small intestine (e.g., duodenum, jejunum, or ileum), or the colon. The tissue wall 90 includes a target site 95 such as a cut, laceration, or other wound. For example, the target site 95 may result from torn or cut tissue, e.g., due to an injury or as part of a medical procedure, such as a biopsy.

The patch 880 may have opposing ends, labeled 880a and 880b, that are applied to areas on either side of the target site 95, and a middle portion 880c between the two ends. The first end 880a may be applied and secured to the tissue wall 90 adjacent to the target site 95, e.g., via natural adhesive properties of the patch 880 or a suitable adhesive applied as discussed above. The patch 880 then may be manipulated to apply the second end 880b to the tissue wall 90 on the opposite side of the target site 95, such that the patch 880 acts to bring the sides of the target site 95 together to close the wound. The patch 880 therefore may have enough structural integrity to withstand manipulation and to secure the sides of the wound together. In some examples, at least a portion of the patch 880 may stretch to facilitate placement and application of the patch 880 to the target site 95. For example, middle portion 880c may be sufficiently resilient to allow for application of the first and second ends 880a, 880b on opposing sides of the target site 95 and then spring back to its original shape to bring the sides of target site 95 together. Each end 880a, 880b may include a suitable adhesive to promote and facilitate attachment of the patch 880 to the tissue wall 90. In some examples, the middle portion 880c of the patch 880 does not include adhesive.

The patch 880 may be delivered to the target site 95 via any suitable method, including, for example, the methods illustrated in the accompanying figures. For example, the patch 880 may be delivered using the system illustrated in FIG. 7, e.g., via an endoscope 700 that may include any of the features of endoscope 100 of FIG. 1. The endoscope shaft 704 includes a working channel 720 that accommodates a delivery instrument 750 equipped with the patch 880, wherein the instrument 750 may include any of the features of instrument 250 of FIGS. 2A-2C. The endoscope 700 includes a second working channel 722 that accommodates a forceps 790. The patch 880 may be released from the instrument 750 by rotating the distal end 754 of instrument 750 relative to the shaft 752. For example, the first end 880a may be pressed to a portion of the tissue 90 adjacent to the target site 95 with sufficient pressure so that it adheres to the tissue 90. Additional rotation may release the remaining portion of the patch 880 from the distal end 754, including second end 880b. Finally, the forceps 790 may be used to grasp the second end 880b of the patch 880 and apply it to the portion of the tissue 90 adjacent to the opposite side of the target site 95. The instrument 750 optionally may be withdrawn into the working channel 720 to provide working space for the forceps 790. In some examples, the endoscope 700 may include only one working channel 720, the instrument 750 being withdrawn from the working channel 720 before introducing the forceps 790 into the same working channel 720.

Other embodiments of the present disclosure will be apparent to those skilled in the art from consideration of the specification and practice of the embodiments disclosed herein. It is intended that the specification and examples be considered as exemplary only, with a true scope and spirit of the present disclosure being indicated by the following claims.

We claim:

1. A method of delivering a patch to a target site of a patient, the method comprising:
   introducing an endoscope into a gastrointestinal tract of a patient, wherein the endoscope includes a patch in a folded or crimped configuration, the patch comprising a biocompatible material;
   positioning a distal end of the endoscope proximate a target site; and
   applying the patch to the target site while releasing the patch from the endoscope;
   wherein the target site includes a laceration in tissue following endoscopic mucosal resection (EMR), endoscopic submucosal dissection (ESD), or tissue biopsy; or wherein the target site includes an anastomosis;

wherein the endoscope includes a cap coupled to the distal end of the endoscope, the patch covering a distal end of the cap and being releasable from the cap;

wherein the patch is secured to an outer surface of the cap with a flexible band; and wherein releasing the patch from the cap includes actuating a wire to cut the flexible band from the cap.

2. The method of claim 1, wherein the patch comprises chitosan, extracellular matrix, or a combination thereof.

3. The method of claim 1, wherein the cap has a frusto-conical shape and a ridge on an outer surface of the cap.

4. The method of claim 1, wherein the distal end of the endoscope includes an optical device, and the patch includes an opening aligned with the optical device.

5. The method of claim 1, wherein the cap is fixedly coupled to the distal end of the endoscope.

6. The method of claim 1, wherein releasing the patch from the cap includes applying pressure to the patch with the endoscope.

7. A method of delivering a patch to a target site of a patient, the method comprising:

introducing a system comprising an endoscope into a gastrointestinal tract of a patient, wherein the system includes a patch comprising a biocompatible material and a cap fixedly coupled to a distal end of the endoscope, wherein the patch is secured to an outer surface of the cap with a flexible band, covers a distal opening of the cap, and is releasable from the cap;

positioning a distal end of the endoscope proximate a target site; and applying the patch to the target site while releasing the patch from cap;

wherein releasing the patch from the cap includes actuating a wire to release the flexible band.

8. The method of claim 7, wherein applying the patch includes blowing air or spraying water from a channel of the endoscope onto the patch.

9. The method of claim 7, wherein releasing the patch from the cap includes actuating the wire to cut the flexible band, and a portion of the flexible band remains tethered to the cap after the flexible band is cut.

10. A medical system comprising:

an endoscope defining at least one working channel;

a patch comprising a biocompatible material; and a cap coupled to a distal end of the endoscope, the patch covering a distal end of the cap and being releasable from the cap;

wherein the patch is secured to an outer surface of the cap with a flexible band;

wherein a wire extending through the at least one working channel is coupled to the flexible band;

wherein the distal end of the endoscope includes an optical device, and the patch includes an opening aligned with the optical device.

* * * * *